(12) United States Patent
Scheible et al.

(10) Patent No.: US 9,271,491 B1
(45) Date of Patent: Mar. 1, 2016

(54) USING COLORED BIOCIDAL MULTI-LAYER STRUCTURE

(71) Applicants: John Joseph Scheible, Fairport, NY (US); Tomas Gerard Patrick McHugh, Webster, NY (US); Alan Richard Priebe, Rochester, NY (US); Ronald Steven Cok, Rochester, NY (US)

(72) Inventors: John Joseph Scheible, Fairport, NY (US); Tomas Gerard Patrick McHugh, Webster, NY (US); Alan Richard Priebe, Rochester, NY (US); Ronald Steven Cok, Rochester, NY (US)

(73) Assignee: EASTMAN KODAK COMPANY, Rochester, NY (US)

( * ) Notice: Subject to any disclaimer, the term of this patent is extended or adjusted under 35 U.S.C. 154(b) by 0 days.

(21) Appl. No.: 14/519,489

(22) Filed: Oct. 21, 2014

(51) Int. Cl.
*A61K 49/00* (2006.01)
*A01N 25/34* (2006.01)
*A01N 25/00* (2006.01)
*A01N 59/20* (2006.01)
*A01N 59/16* (2006.01)
*B08B 7/00* (2006.01)

(52) U.S. Cl.
CPC ............... *A01N 25/34* (2013.01); *A01N 25/00* (2013.01); *A01N 59/16* (2013.01); *A01N 59/20* (2013.01); *B08B 7/0014* (2013.01)

(58) Field of Classification Search
CPC ............ A01N 25/34; B05D 3/108; B05D 3/12
USPC ................................. 424/10.3, 10.31
See application file for complete search history.

(56) References Cited

U.S. PATENT DOCUMENTS

| | | | |
|---|---|---|---|
| 5,662,991 A | 9/1997 | Smolik et al. | |
| 5,980,620 A | 11/1999 | Brodie et al. | |
| 6,437,021 B1 | 8/2002 | Wettling et al. | |
| 7,143,709 B2 | 12/2006 | Brennan et al. | |
| 7,579,396 B2 | 8/2009 | Blanton et al. | |
| 2006/0293205 A1* | 12/2006 | Chung | C11D 3/40 510/383 |
| 2008/0242794 A1 | 10/2008 | Sandford et al. | |
| 2009/0291147 A1 | 11/2009 | Sandford et al. | |
| 2010/0034900 A1 | 2/2010 | Temchenko et al. | |
| 2010/0093851 A1 | 4/2010 | Blanton et al. | |
| 2010/0160486 A1 | 6/2010 | Blanton et al. | |
| 2014/0170298 A1 | 6/2014 | Terry et al. | |

* cited by examiner

*Primary Examiner* — Roberts Culbert
(74) *Attorney, Agent, or Firm* — Raymond L. Owens

(57) ABSTRACT

A method of using a colored biocidal multi-layer structure includes locating the colored biocidal multi-layer structure on a surface, observing the colored biocidal multi-layer structure over time, and observing a change in the color in at least a portion of the colored biocidal multi-layer structure, indicating that the colored biocidal multi-layer structure is less effective. The colored biocidal multi-layer structure includes a first layer of a first color, and a biocidal second layer on or over the first layer, the biocidal second layer of a second color different from the first color.

16 Claims, 7 Drawing Sheets

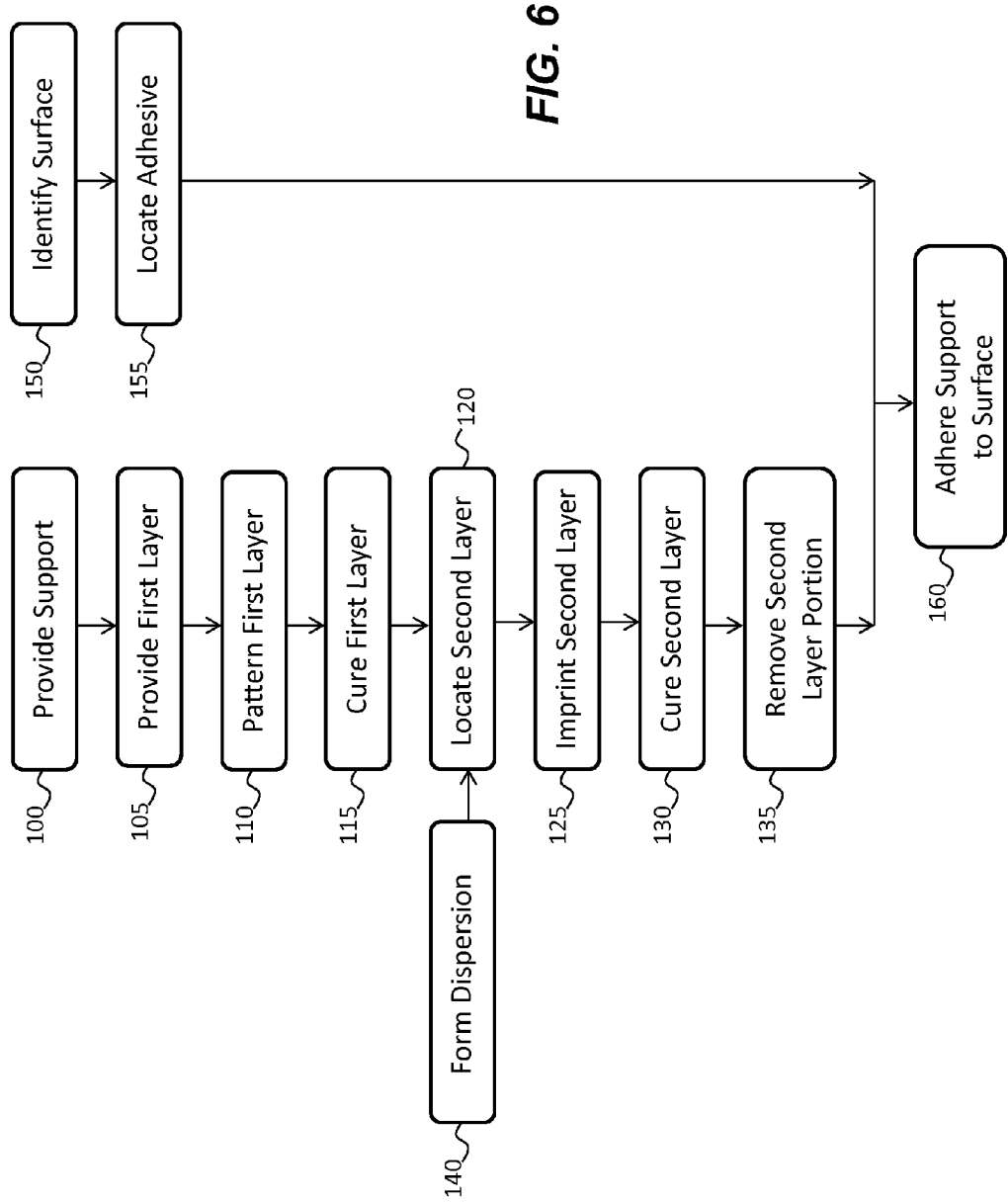

USING COLORED BIOCIDAL MULTI-LAYER STRUCTURE

CROSS REFERENCE TO RELATED APPLICATIONS

Reference is made to commonly-assigned U.S. patent application Ser. No. 14/519,425, filed Oct. 21, 2014, entitled Colored Biocidal Multi-Layer Structure, by Scheible et al, and to commonly-assigned U.S. patent application Ser. No. 14/519,451, filed Oct. 21, 2014, entitled Making Colored Biocidal Multi-Layer Structure, by Scheible et al, to commonly-assigned U.S. patent application Ser. No. 13/235,789, (now U.S. Publication No. 2013/0071143), filed Sep. 19, 2011, entitled Antibacterial and Antifungal Protection for Toner Image, by Blanton et al, and to commonly-assigned U.S. patent application Ser. No. 13/357,082, (now U.S. Publication No. 2013/0186301), filed Jan. 24, 2012, entitled Ink Having Antibacterial and Antifungal Protection, by Blanton et al, the disclosures of which are incorporated herein.

FIELD OF THE INVENTION

The present invention relates to biocidal layers having antimicrobial efficacy on a surface.

BACKGROUND OF THE INVENTION

Widespread attention has been focused in recent years on the consequences of bacterial and fungal contamination contracted by contact with common surfaces and objects. Some noteworthy examples include the sometimes fatal outcome from food poisoning due to the presence of particular strains of *Escherichia coli* in undercooked beef; *Salmonella* contamination in undercooked and unwashed poultry food products; as well as illnesses and skin irritations due to *Staphylococcus aureus* and other micro-organisms. Anthrax is an acute infectious disease caused by the spore-forming bacterium *bacillus anthracis*. Allergic reactions to molds and yeasts are a major concern to many consumers and insurance companies alike. In addition, significant fear has arisen in regard to the development of antibiotic-resistant strains of bacteria, such as methicillin-resistant *Staphylococcus aureus* (MRSA) and vancomycin-resistant *Enterococcus* (VRE). The U.S. Centers for Disease Control and Prevention estimates that 10% of patients contract additional diseases during their hospital stay and that the total deaths resulting from these nosocomially-contracted illnesses exceeds those suffered from vehicular traffic accidents and homicides. In response to these concerns, manufacturers have begun incorporating antimicrobial agents into materials used to produce objects for commercial, institutional, residential, and personal use.

Noble metal ions such as silver and gold ions are known for their antimicrobial properties and have been used in medical care for many years to prevent and treat infection. In recent years, this technology has been applied to consumer products to prevent the transmission of infectious disease and to kill harmful bacteria such as *Staphylococcus aureus* and *Salmonella*. In common practice, noble metals, metal ions, metal salts, or compounds containing metal ions having antimicrobial properties can be applied to surfaces to impart an antimicrobial property to the surface. If, or when, the surface is inoculated with harmful microbes, the antimicrobial metal ions or metal complexes, if present in effective concentrations, will slow or even prevent altogether the growth of those microbes. Recently, silver sulfate, $Ag_2SO_4$, described in U.S. Pat. No. 7,579,396, U.S. Patent Application Publication 2008/0242794, U.S. Patent Application Publication 2009/0291147, U.S. Patent Application Publication 2010/0093851, and U.S. Patent Application Publication 2010/0160486 has been shown to have efficacy in providing antimicrobial protection in polymer composites. The United States Environmental Protection Agency (EPA) evaluated silver sulfate as a biocide and registered its use as part of EPA Reg. No, 59441-8 EPA EST. NO. 59441-NY-001. In granting that registration, the EPA determined that silver sulfate was safe and effective in providing antibacterial and antifungal protection.

Antimicrobial activity is not limited to noble metals but is also observed in other metals such as copper and organic materials such as triclosan, and some polymeric materials.

It is important that the antimicrobial active element, molecule, or compound be present on the surface of the article at a concentration sufficient to inhibit microbial growth. This concentration, for a particular antimicrobial agent and bacterium, is often referred to as the minimum inhibitory concentration (MIC). It is also important that the antimicrobial agent be present on the surface of the article at a concentration significantly below that which can be harmful to the user of the article. This prevents harmful side effects of the article and decreases the risk to the user, while providing the benefit of reducing microbial contamination. There is a problem in that the rate of release of antimicrobial ions from antimicrobial films can be too facile, such that the antimicrobial article can quickly be depleted of antimicrobial active materials and become inert or non-functional. Depletion results from rapid diffusion of the active materials into the biological environment with which they are in contact, for example, water soluble biocides exposed to aqueous or humid environments. It is desirable that the rate of release of the antimicrobial ions or molecules be controlled such that the concentration of antimicrobials remains above the MIC. The concentration should remain there over the duration of use of the antimicrobial article. The desired rate of exchange of the antimicrobial can depend upon a number of factors including the identity of the antimicrobial metal ion, the specific microbe to be targeted, and the intended use and duration of use of the antimicrobial article.

Antimicrobial coatings are known in the prior art, for example as described in U.S. Patent Application Publication No. 2010/0034900. This disclosure teaches a method of coating a substrate with biocide particles dispersed into a coating so that the particles are in contact with the environment. Non-planar coatings are also known to provide surface topographies for non-toxic bio-adhesion control, for example as disclosed in U.S. Pat. No. 7,143,709.

Fabrics or materials incorporating biocidal elements are known in the art and commercially available. U.S. Pat. No. 5,662,991 describes a biocidal fabric with a pattern of biocidal beads. U.S. Pat. No. 5,980,620 discloses a means of inhibiting bacterial growth on a coated substrate comprising a substantially dry powder coating containing a biocide. U.S. Pat. No. 6,437,021 teaches a water-insoluble polymeric support containing a biocide. Methods for depositing thin silver-comprising films on non-conducting substrates are taught in U.S. Patent Application Publication No. 2014/0170298.

However, as noted above, the antimicrobial coatings and materials lose their efficacy over time. Due to the variety of environmental circumstances and usage patterns of such antimicrobial coatings and materials, it is difficult to know when they are no longer efficacious.

SUMMARY OF THE INVENTION

There is a need, therefore, for an anti-microbial article that is readily replaced or refreshed in response to a simply observed indication incorporated into the anti-microbial article.

In accordance with the present invention, a method of using a colored biocidal multi-layer structure includes:

locating the colored biocidal multi-layer structure on a surface;

observing the colored biocidal multi-layer structure over time;

observing a change in the color in at least a portion of the colored biocidal multi-layer structure, indicating that the colored biocidal multi-layer structure is less effective; and wherein the colored biocidal multi-layer structure includes a first layer of a first color, and a biocidal second layer on or over the first layer, the biocidal second layer of a second color different from the first color.

The present invention provides a colored biocidal multi-layer structure that provides antimicrobial properties and is readily refreshed or replaced in response to a simply observed indication.

BRIEF DESCRIPTION OF THE DRAWINGS

The above and other features and advantages of the present invention will become more apparent when taken in conjunction with the following description and drawings wherein identical reference numerals have been used to designate identical features that are common to the figures, and wherein:

FIGS. 6-8 are flow diagrams illustrating methods of the present invention.

The Figures are not drawn to scale since the variation in size of various elements in the Figures is too great to permit depiction to scale.

DETAILED DESCRIPTION OF THE INVENTION

Figure 1:
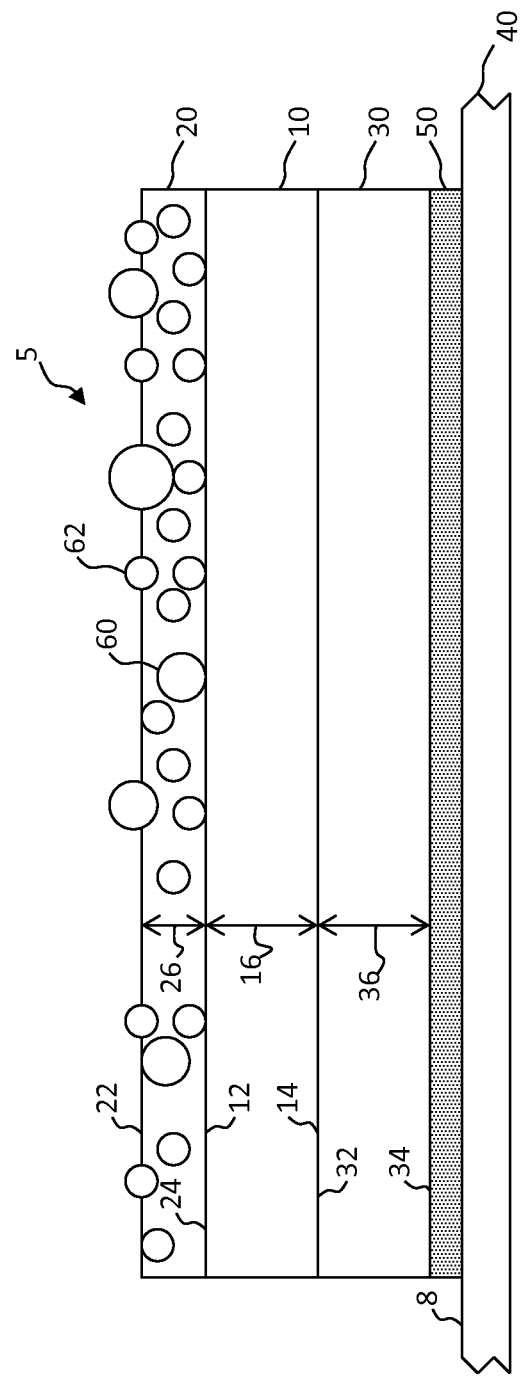
FIG. 1 is a cross section illustrating an embodiment of the present invention.

The present invention provides an antimicrobial article such as a bi-layer biocidal structure 5 shown in FIG. 1 of the present invention that includes a simply observed indication to replace the article. In an embodiment, the indication is related, either directly or indirectly, to the antimicrobial efficacy of the article or is otherwise associated with the antimicrobial efficacy of the article. The indication is provided by apparent changes in color of at least portions of the article. The changes are, for example, patterns, text, or graphic elements formed in an underlying layer that are exposed as overlying layers exposed to the environment are degraded over time. In one method of the present invention, the antimicrobial article is repeatedly washed and the repeated washing removes portions of the article to expose the indication and indicate that the article should be replaced.

Referring to FIG. 1, in an embodiment of the present invention, the biocidal multi-layer structure 5 includes a first layer 10 of a first color and a biocidal second layer 20 on or over the first layer 10. The biocidal second layer 20 has a second color different from the first color. Any layers, for example adhesive or environmental protection layers, located between the first layer 10 and the second layer 20 are sufficiently transparent that the color of the first layer 10 is perceived by an observer through the second layer 10. In an embodiment, the first or second layers 10, 20 are polymer or contain polymers, for example polymers coated as a liquid or laminated and then cured with heat, drying, or radiation.

In an embodiment, the first layer 10 is located on or over a support 30, for example a substrate such as glass or plastic. In a useful arrangement, the support 30 is adhered, for example with an adhesive layer 50 such as a pressure-sensitive adhesive or glue such as wall-paper glue, to a surface 8. The surface 8 is any surface 8, planar or non-planar that is desired to resist the growth of biologically undesirable organisms, including microbes, bacteria, or fungi. In various applications, the surface 8 is a surface of a structure 40, such as a wall, floor, table top, door, handle, cover, device surface, or any surface likely to come into contact with a human.

The support 30 is any layer that is capable of supporting the first and second layers 10, 20 and in different embodiments is rigid, flexible, or transparent and is made of a plastic, paper, or vinyl or combinations of materials. The support 30 has a support thickness 36 measured from a first support side 32 to an opposing second support side 34 that can, for example be adhered to the surface 8. The biocidal multi-layer structure 5 can form a wall paper.

The first layer 10 has a first-layer thickness 16 measured from a first-layer first side 12 to an opposing first-layer second side 14 that is, for example, adhered to the first support side 32. The biocidal second layer 20 has a second-layer thickness 26 measured from a second-layer first side 22 to an opposing second-layer second side 24 that is, for example, adhered or cross linked to the first-layer first side 12. Alternatively, an adhesion layer such as a binder primer layer 52 (FIG. 2) is located between the first and second layers 10, 20 to adhere the first and second layers 10, 20 together.

The biocidal second layer 20 is a biocidal layer. By biocidal layer is meant herein any layer that resists the growth of undesirable biological organisms, including microbes, bacteria, or fungi or more generally, eukaryotes, prokaryotes, or viruses. In particular, the biocidal second layer 20 resists the growth, reproduction, or life of infectious micro-organisms that cause illness or death in humans and especially antibiotic-resistant strains of bacteria. In various embodiments, the biocidal second layer 20 is rendered biocidal by including chemicals such as drugs in the biocidal second layer 20 or by including particles 60 such as ionic metals or metal salts in the biocidal second layer 20. The particles 60 reside in the biocidal second layer 20. In an embodiment, some of the particles 60 in the biocidal second layer 20 are exposed particles 62 that extend from the second-layer first side 22 into the environment and can interact with any environmental contaminants or biological organisms in the environment. Exposed particles 62 are thus more likely to be efficacious in destroying microbes. In various embodiments, the particles 60 are silver or copper, are a metal sulfate, have a silver component, are a salt, have a sulfur component, have a copper component, are a silver sulfate salt, or include phosphors. In an embodiment, the biocidal second layer 20 is thinner than the first layer 10 so that the second-layer thickness 26 is less than the first-layer thickness 16, thus reducing the quantity of particles 60 or drugs that are required in the biocidal second layer 20. In an alternative embodiment, the second-layer thickness 26 is greater than the first-layer thickness 16.

Figure 2:
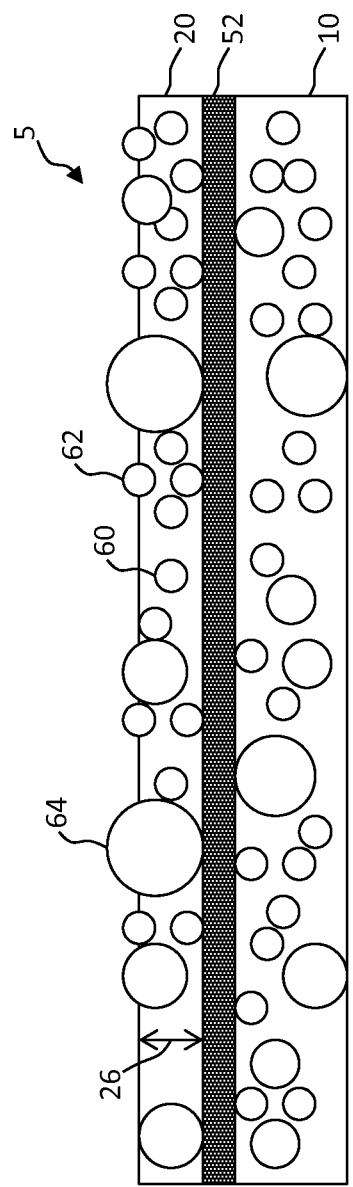
FIG. 2 is a cross section of a multi-layer structure in another embodiment of the present invention.

Referring further to FIG. 2, the particles 60 of the bi-layer biocidal structure 5 in the biocidal second layer 20 have a variety of sizes, for example some particles are large particles 64, others are smaller particles 60, and some of either are exposed particles 62. The particles 60 include both the large particles 64 and any exposed particles 62. In an embodiment, the biocidal second layer 20 has a second-layer thickness 26 that is less than at least one diameter of one or more of the particles 60, has a second-layer thickness 26 that is less than a mean diameter of the particles 60, or has a second-layer thickness 26 that is less than the median diameter of the particles 60. In another embodiment, the particles 62 have at least one diameter between 0.05 and 25 microns. Suitable particles with such a size range have been made. Alternatively, the biocidal second layer 20 is greater than or equal to 0.5 microns thick and the biocidal second layer 20 is less than or equal to 20 microns thick. When the second-layer thickness 26 is less than the diameter of a substantial number of particles 60, some of the particles 60 are not necessarily exposed particles 62.

In another embodiment and as shown in FIG. 2, the first layer 10 includes particles 60. Alternatively, both the first layer 10 and the biocidal second layer 20 include particles 60 and the particles 60 in the first layer 10 are the same kind of particles 60 as the particles 60 in the biocidal second layer 20.

Figure 3:
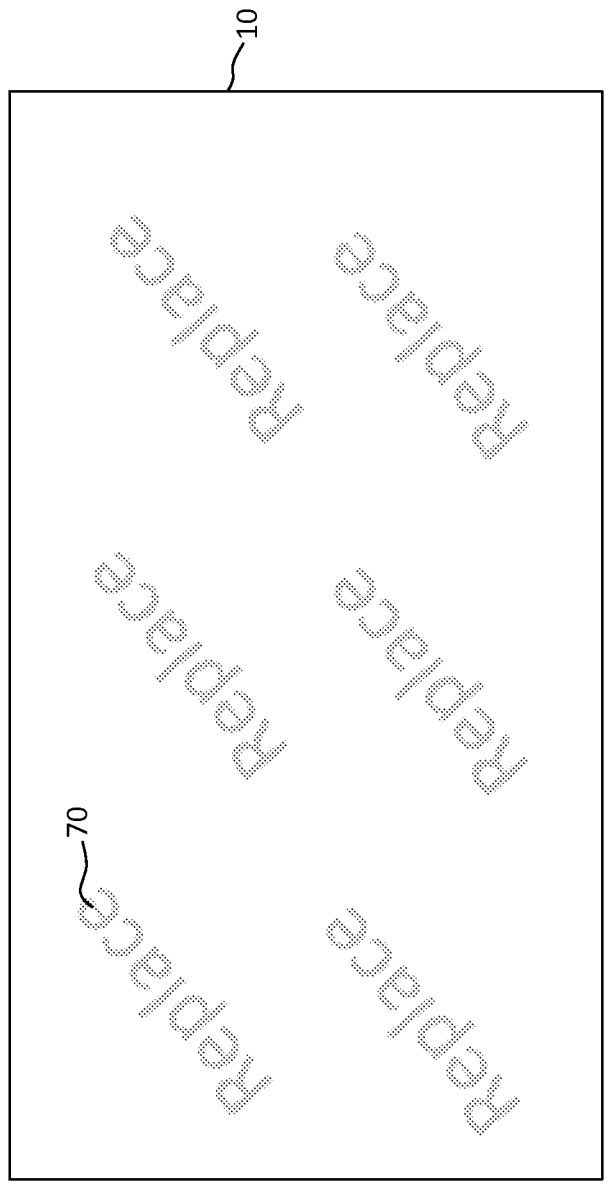
FIGS. 3 and 4 are plan views of a layer useful in embodiments of the present invention.
Figure 4:
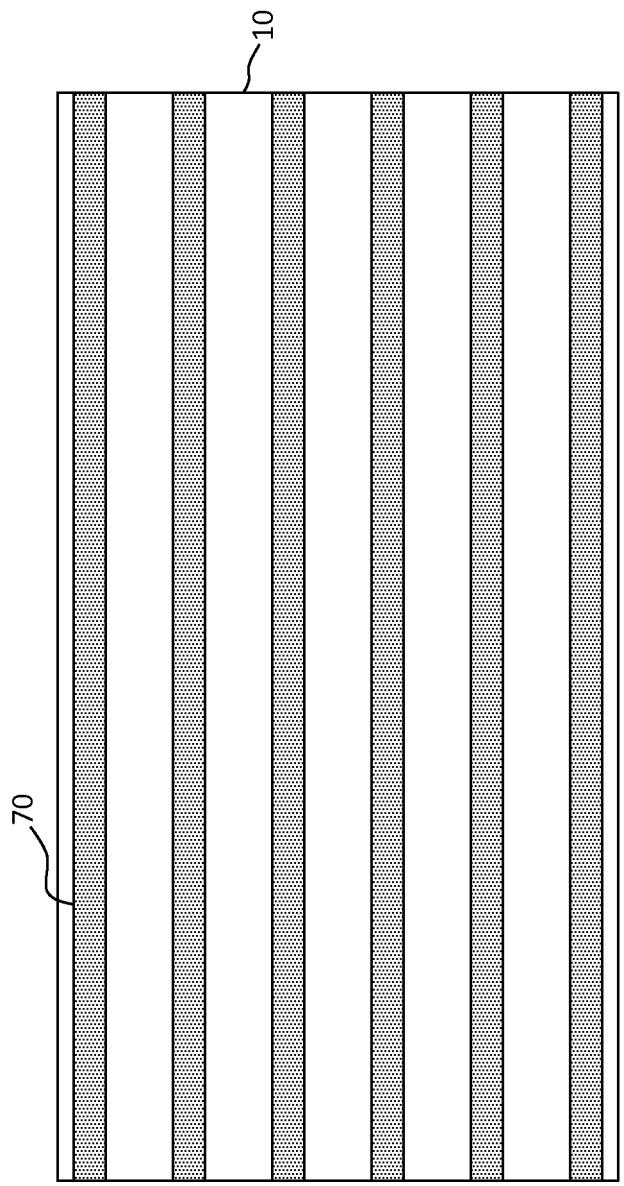

Referring to FIGS. 3 and 4, according to embodiments of the present invention, the first layer 10 is patterned or has an indicator 70. The indicator 70 or pattern can be text (for example the word "Replace"), graphic elements, pictograms, or pictures. In an embodiment, the patterning or indicator 70 is a patterning having the first color. Alternatively, the first layer 10 simply has a different first color from the second color and the different color indicates that the biocidal second layer 20 should be replaced. Since the biocidal second layer 20 can, over time, become ineffective and need to be replaced, the first color, the pattern or the indicator 70 indicates that the biocidal second layer 20 should be replaced.

In various embodiments, the first color is red (a color of alarm or emergency in many cultures), is darker than the second color (since darker colors are associated with dirt in medical environments), or is black or gray. Alternatively or in addition, for similar reasons in some embodiments the second color is lighter than the first color or is a color associated in some cultures with cleanliness or purity, such as white, blue, or green.

Figure 5:
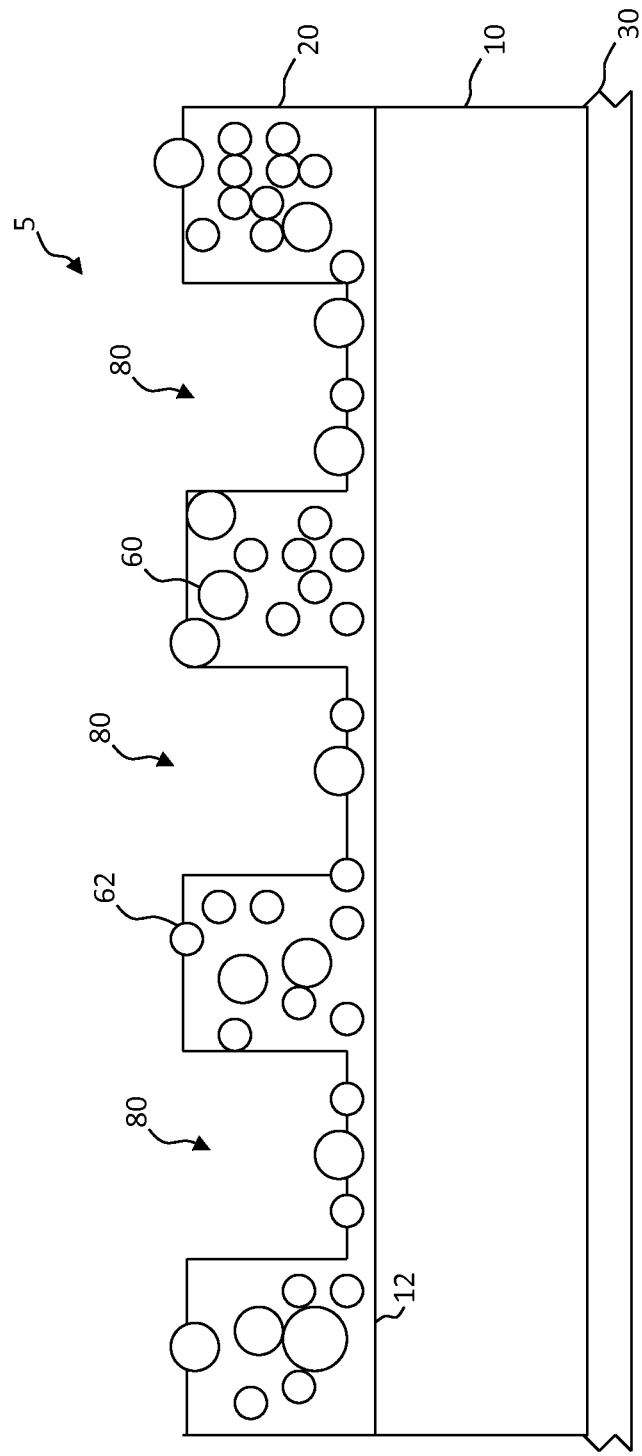
FIG. 5 is a cross section of a non-planar embodiment of the present invention.

Referring to FIG. 5, in an embodiment the biocidal second layer 20 is non-planar. Such non-planar layers are made in curable polymer layers with a stamp using imprinting methods known in the art. As shown in FIG. 5, the first and second layers 10, 20 are formed on the support 30. The non-planar second layer includes the particles 60 and the exposed particles 62 and has indentations 80. The indentations 80 form a topographical non-planar layer in the biocidal second layer 20 that is inhospitable to the growth and reproduction of microbes. In yet another embodiment, the first or second layers 10, 20 have a hydrophobic surface, for example by providing a roughened surface either by imprinting or by a treatment such as sandblasting or exposure to energetic gases or plasmas.

In a further embodiment of the present invention, the first layer 10, the biocidal second layer 20, or the support 30 is or includes a heat-shrink film, for example polyolefin, polyvinylchloride, polyethylene, or polypropylene. Any of the first layer 10, the biocidal second layer 20, or the support 30 can include cross linking materials that are cross linked for example by radiation or heat to provide strength.

FIG. 6 is a flow chart illustrating various methods of the present invention. Referring to FIG. 6, a method of making a colored biocidal multi-layer structure 5 includes providing the support 30 in step 100 and forming the first layer 10 on the support 30 in step 105. In one embodiment, the support 30 and first layer 10 are the same structure provided as a single element. The first layer 10 has a first color. In an optional embodiment, the first color is patterned in the first layer 10 in step 110, for example forming text, graphics, graphic elements, pictures, or pictograms. In various embodiments, the support 30 is paper or plastic and the first layer 10 is plastic, for example a polymer or a cross linkable polymer that is curable. The first layer 10 is patterned in any of a variety of ways known in the art, for example by printing with ink transfer from a patterned surface or by inkjet patterning. The first layer 10 is formed in various ways, including extrusion or coating, for example spin coating, curtain coating, or hopper coating, or other methods known in the art. The first layer 10 is cured, if necessary, for example by heat or radiation in step 115.

The biocidal second layer 20 is also formed in various methods known in the art and is a biocidal layer that includes biocidal materials such as drugs, biocides, or particles 60. The biocidal second layer 20 has a second color different from the first color. In an embodiment, a dispersion of particles 60 is formed in a carrier such as a liquid in step 140 and located on the cured first layer 10 in step 120, for example by coating, to form the biocidal second layer 20. Making and coating liquids with dispersed particles is known in the art. In an alternative, the biocidal second layer 20 is made separately and laminated on or over the first layer 10.

Optionally, the biocidal second layer 20 is imprinted in step 125 and cured in step 130 to form the non-planar biocidal second layer 20 including biocidal particles 60. Imprinting methods are known in the art and employ a stamp pressed against an uncured layer that is then cured and the stamp removed. Again optionally, a portion of the biocidal second layer 20 is removed in step 135, for example to expose the particles 60 to form exposed particles 62 or increase the surface area of the exposed particles 62 that is exposed. Removal of portions of the biocidal second layer 20 is accomplished in step 135, for example, by exposing the biocidal second layer 20 and particles 60 to energetic particles such as gases or plasma, for example using processes such as etching, plasma etching, reactive plasma etching, ion etching, or sandblasting. Such removal methods are known in the art. In other embodiments, the biocidal second layer 20 is formed, imprinted, and treated before it is located on or over the first layer 10, for example by lamination.

In step 150, a surface 8 is identified. The surface 8 is a surface which it is desired to keep free of microbes, for example a wall, floor, table top, door, handle, knob, cover, or device surface, especially any surface found in a any type of medical institution. In an embodiment, the surface 8 is planar; in another embodiment, the surface 8 is non-planar. In step 155, an adhesive is located, for example on the surface 8 or on the second support side 34 of the support 30 opposite the surface 8, to form an adhesive layer 50. The support 30 is adhered to the surface 8 in step 160. In a further embodiment, the support 30, first layer 10, and biocidal second layer 20 are heated to shrink the layers on the surface 8 if the surface 8 is non-planar. In an embodiment, the heating step (not shown separately) is also the adhesion step 160 and a separate adhesive layer 50 is not necessary or used. In an embodiment, the biocidal second layer 20 is thinner than the first layer 10. In another embodiment, the biocidal second layer 20 is formed to have a thickness such that the particles 60 extend from a surface (e.g. second-layer first side 22) of the biocidal second layer 20 and a portion of the particle's surface area is exposed. For example, the biocidal second layer 20 is formed with a thickness that is less than at least one diameter of one or more of the particles 60, has a thickness that is less than a mean diameter of the particles 60, or has a thickness that is less than the median diameter of the particles 60.

In a further embodiment, the first layer 10 is a biocidal first layer 10 and includes drugs or anti-microbial particles 60. In such an embodiment, the first layer 10 is formed as a dispersion with particles or a liquid with multiple components that are coated over the support 30 or formed into a layer that is laminated to the support 30 or formed into a free-standing layer on which the biocidal second layer 20 is located. In an alternative, the biocidal second layer 20 includes one or more particles 60 in a liquid and the particles 60 self-segregate in the liquid before the liquid is cured. In an embodiment, the particles 60 self-segregate after the liquid is coated, for example over or on first layer 10, and before the liquid is cured to form the biocidal second layer 20. In another embodiment, the self-segregating particles aggregate at the second-layer first side 22 of the biocidal second layer 20.

In another embodiment, the first layer 10 includes one or more particles 60, and a method of the present invention further includes forming the first layer 10 so that the particles 60 extend from a portion of the surface of the first layer 10 and are exposed and optionally further including removing a portion of the first layer surface and increasing the exposed surface area of the particles 60, for example by etching, plasma etching, reactive plasma etching, ion etching, or sandblasting.

Figure 7:
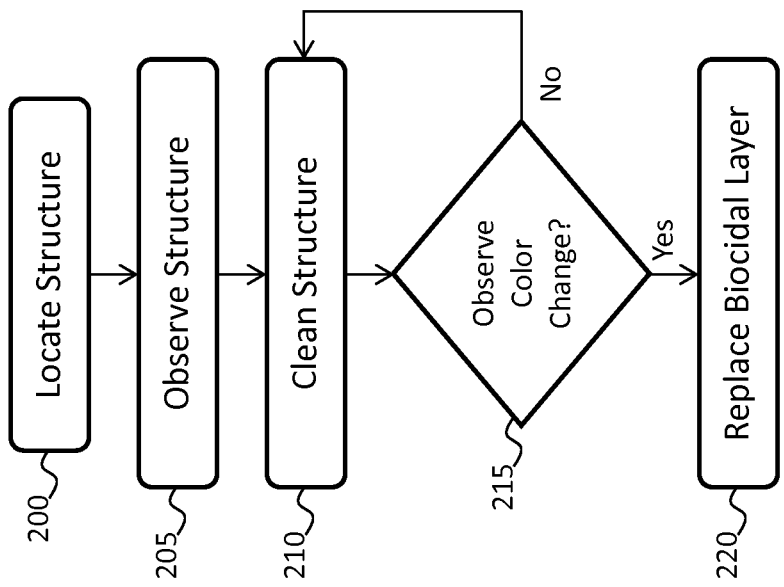

Referring to FIG. 7, in another method of the present invention, the colored biocidal multi-layer structure 5 is used by first locating the structure in step 200, for example on the surface 8 on which it is desired to inhibit the presence of microbes. The colored biocidal multi-layer structure 5 is observed over time in step 205, especially with respect to the structure's color or appearance and the visibility of the patterns described above (e.g. as shown in FIGS. 3 and 4). The colored biocidal multi-layer structure 5 and especially the biocidal second layer 20 is periodically cleaned in step 210 to remove dirt and any microbes, alive or dead, on the surface (e.g. second-layer first side 22) of the biocidal second layer 20. According to various embodiments of the present invention, the cleaning process of step 210 gradually abrades or dissolves the biocidal second layer 20 so that over time the biocidal second layer 20 is at least partially removed and the first color or patterning of the first layer 10 is revealed. As long as the biocidal second layer 20 remains sufficiently in place, no color or pattern change is observed in step 215 and the periodic cleaning continues. Eventually, the color change is observed in step 215 and the biocidal layer 20 is replaced in step 220.

Replacement can proceed in a variety of ways. According to various embodiments of the present invention, the colored biocidal multi-layer structure 5, or portions of the colored biocidal multi-layer structure 5 are replaced when the first color of the first layer 10 becomes apparent. In one embodiment, another colored biocidal multi-layer structure 5 is simply located over the colored biocidal multi-layer structure 5. Thus, the colored biocidal multi-layer structure 5 becomes the structure 40 and another colored biocidal multi-layer structure 5 is applied to the structure 40, for example with an adhesive layer 50 (FIG. 1). In another embodiment, the colored biocidal multi-layer structure 5 is removed and another colored biocidal multi-layer structure 5 put in its place. As shown in FIG. 1, the support 30 is adhered to the structure 40 with an adhesive layer 50. Chemical or heat treatments are applied to the colored biocidal multi-layer structure 5 to loosen, dissolve, or remove the adhesive layer 50 so the colored biocidal multi-layer structure 5 can be removed and another adhesive layer 50 is applied to the structure 40. In an embodiment, the colored biocidal multi-layer structure 5 is peeled from the structure 40 and another colored biocidal multi-layer structure 5 having an adhesive layer 50 on the third-layer second support side 34 adhered to the structure 40.

Alternatively, portions of the colored biocidal multi-layer structure 5 are removed, for example at least a portion of the biocidal second layer 20 is mechanically separated from the first layer 10. In an embodiment, the biocidal second layer 20 is peeled from the first layer 10. Alternatively, the biocidal second layer 20 is abraded and removed by abrasion from the first layer 10. As the biocidal second layer 20 is removed, the first color, pattern, or indicator 70 of the first layer 10 becomes increasingly visible. In another embodiment, the biocidal second layer 20 is chemically separable from the first layer 10 or chemically dissolvable in a substance that does not dissolve the first layer 10. In a useful embodiment, a substance that chemically separates the biocidal second layer 20 from the first layer 10 or that chemically dissolves the biocidal second layer 20 is a cleaning agent. In an embodiment, the biocidal second layer 20 is repeatedly cleaned, for example by spraying the biocidal second layer 20 with a cleaning agent and then rubbing or wiping the biocidal second layer 20, and at each cleaning a portion of the biocidal second layer 20 is removed to gradually expose the first layer 10, the first color of the first layer 10, and the indicator 70.

Figure 8:
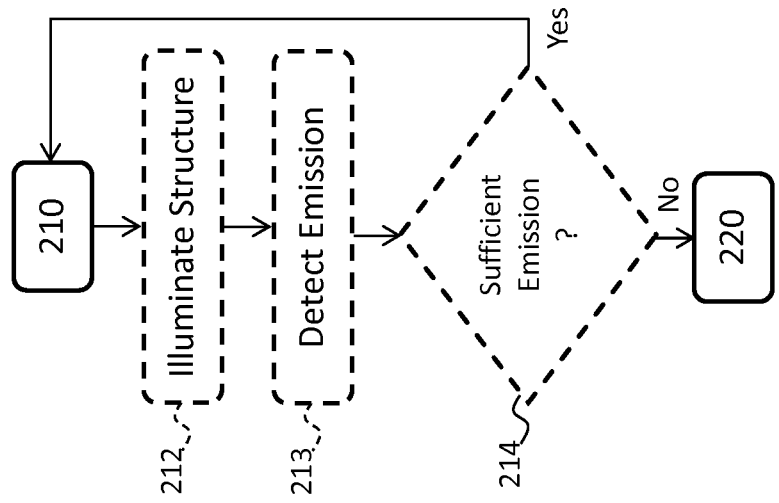

Referring to FIG. 8 in another embodiment of the present invention, fluorescent or phosphorescent materials are included in the biocidal second layer 20 and are illuminated in step 212. The fluorescent or phosphorescent materials respond to ultra-violet, visible, or infrared illumination and emit light that can be seen or detected in step 213 and compared to a threshold emission value in step 214. Thus, the continuing presence of the biocidal second layer 20 is observed. When light emission in response to illumination is no longer present at a desired level, the biocidal second layer 20 is replaced.

According to yet another embodiment of the present invention, the cleaning step 215 refreshes the biocidal second layer 20 so that the exposed particles 60 in the biocidal second layer 20 are more efficacious. This can be done, for example, by ionizing the particles 70, by removing oxidation layers on the particles 60, or by removing extraneous materials such as dust from the particles 70.

Useful cleaners include hydrogen peroxide, for example 2% hydrogen peroxide, water, soap in water, or a citrus-based cleaner. In an embodiment, the 2% hydrogen peroxide solution is reactive to make oxygen radicals that improve the efficacy of particles 60. In various embodiments, cleaning is accomplished by spraying the second-layer first side 22 of the biocidal second layer 20 with a cleaner and then wiping or rubbing the second-layer first side 22. The cleaner can dissolve the biocidal second layer 20 material and the wiping or rubbing can remove dissolved material or abrade the second-layer first side 22 of the biocidal second layer 20 to expose other particles 60 or increase the exposed surface area of exposed particles 62.

The present invention is useful in a wide variety of environments and on a wide variety of surfaces 8, particularly surfaces 8 that are frequently handled by humans. The present invention can reduce the microbial load in an environment and is especially useful in medical facilities.

The invention has been described in detail with particular reference to certain embodiments thereof, but it will be understood that variations and modifications can be effected within the spirit and scope of the invention.

PARTS LIST

- 5 bi-layer biocidal structure
- 8 surface
- 10 first layer
- 12 first-layer first side
- 14 first-layer second side
- 16 first-layer thickness
- 20 second layer
- 22 second-layer first side
- 24 second-layer second side
- 26 second-layer thickness
- 30 support
- 32 first support side
- 34 second support side
- 36 support thickness
- 40 structure
- 50 adhesive layer
- 52 binder primer
- 60 particle
- 62 exposed particle
- 64 large particle
- 70 indicator
- 80 indentations
- 100 provide support step
- 105 provide first layer step
- 110 pattern first layer step
- 115 cure first layer step
- 120 locate second layer step
- 125 imprint second layer step
- 130 cure second layer step

PARTS LIST (CON'T)

- 135 remove second layer portion step
- 140 form dispersion step
- 150 identify surface step
- 155 locate adhesive step
- 160 adhere support to surface step
- 200 locate structure step
- 205 observe structure step
- 210 clean structure step
- 212 illuminate structure step
- 213 sufficient emission comparison step
- 214 detect emission step
- 215 observe color change step
- 220 replace biocidal layer step

The invention claimed is:

1. A method of using a colored biocidal multi-layer structure, comprising:
   locating the colored biocidal multi-layer structure on a surface;
   observing the colored biocidal multi-layer structure over time;
   observing a change in the color in at least a portion of the colored biocidal multi-layer structure, indicating that the colored biocidal multi-layer structure is less effective; and
   wherein the colored biocidal multi-layer structure includes a first layer of a first color, and a biocidal second layer on or over the first layer, the biocidal second layer of a second color different from the first color.

2. The method of claim 1, further including locating another biocidal layer over the first layer.

3. The method of claim 1, further including removing at least a portion of the biocidal second layer and locating another biocidal layer over the remaining biocidal structure.

4. The method of claim 1, further including replacing the colored biocidal multi-layer structure on the surface.

5. The method of claim 1, further including cleaning the colored biocidal multi-layer structure.

6. The method of claim 1, further including changing the color of the colored biocidal multi-layer structure by cleaning the colored biocidal multi-layer structure.

7. The method of claim 1, further including changing the color of the colored biocidal multi-layer structure by abrading the biocidal second layer.

8. The method of claim 1, further including changing the color of the colored biocidal multi-layer structure by chemically modifying or dissolving the biocidal second layer.

9. The method of claim 1, further including laminating a second biocidal second layer on or over the colored biocidal multi-layer structure.

10. The method of claim 1, further including mechanically peeling the biocidal second layer.

11. The method of claim 1, further including replacing the biocidal second layer.

12. The method of claim 1, further including locating a second biocidal second layer over or on the colored biocidal multi-layer structure.

13. The method of claim 1, further including illuminating the colored biocidal multi-layer structure and observing a response of the colored biocidal multi-layer structure to the illumination.

14. The method of claim 1, further including illuminating the colored biocidal multi-layer structure with ultraviolet radiation and observing a response of the colored biocidal multi-layer structure to the ultraviolet radiation.

15. The method of claim 1, further including treating the colored biocidal multi-layer structure to a material to enhance the biocidal efficacy of the colored biocidal multi-layer structure.

16. The method of claim 1, further including heating the colored biocidal multi-layer structure to remove it from the surface.

* * * * *